(12) United States Patent
Yang et al.

(10) Patent No.: US 10,900,130 B2
(45) Date of Patent: Jan. 26, 2021

(54) FUEL PREPARATION REACTION SYSTEM, PEAK REGULATION SYSTEM FOR POWER GENERATION PLANT AND POWER GENERATION PLANT

(71) Applicant: HEPU ENERGY ENVIRONMENIAL TECHNOLOGY CO., LTD., Beijing (CN)

(72) Inventors: Yusen Yang, Beijing (CN); Hua Cui, Beijing (CN); Bo Xu, Beijing (CN); Zhi Tan, Beijing (CN); Hui Chen, Beijing (CN); Wang Zhan, Beijing (CN); Chao Chen, Beijing (CN); Mingzhi Zhu, Beijing (CN)

(73) Assignee: HEPU ENERGY ENVIRONMENTAL TECHNOLOGY CO., LTD., Beijing (CN)

( * ) Notice: Subject to any disclaimer, the term of this patent is extended or adjusted under 35 U.S.C. 154(b) by 0 days.

(21) Appl. No.: 16/627,278

(22) PCT Filed: Aug. 30, 2017

(86) PCT No.: PCT/CN2017/099592
§ 371 (c)(1),
(2) Date: Dec. 27, 2019

(87) PCT Pub. No.: WO2019/000622
PCT Pub. Date: Jan. 3, 2019

(65) Prior Publication Data
US 2020/0131648 A1    Apr. 30, 2020

(30) Foreign Application Priority Data
Jun. 29, 2017    (CN) .......................... 2017 1 0516756

(51) Int. Cl.
*C25B 1/02* (2006.01)
*C25B 15/02* (2006.01)
(Continued)

(52) U.S. Cl.
CPC .............. *C25B 1/02* (2013.01); *C07C 29/151* (2013.01); *C25B 15/02* (2013.01); *H02J 3/28* (2013.01); *H02J 15/00* (2013.01); *C07C 31/04* (2013.01)

(58) Field of Classification Search
CPC ..... H02J 3/00; H02J 3/28; H02J 15/00; Y02E 60/00; Y02E 60/30; Y02E 60/36;
(Continued)

(56) References Cited

U.S. PATENT DOCUMENTS 9,175,199 B2 * 11/2015 Meyer-Pittroff ......... C09K 5/04
2012/0079767 A1   4/2012 Aplin
2012/0091730 A1   4/2012 Stuermer

FOREIGN PATENT DOCUMENTS

CN    101741083 A    6/2010
CN    202596893 U    12/2012
(Continued)

OTHER PUBLICATIONS

International Search Report in the international application No. PCT/CN2017/099592, dated Nov. 1, 2017.
(Continued)

*Primary Examiner* — Natasha E Young
(74) *Attorney, Agent, or Firm* — Syncoda LLC; Feng Ma

(57) ABSTRACT

A fuel preparation reaction system includes: an electrolytic hydrogen production equipment connected to a power supply device of a power generation plant and configured to produce hydrogen through electrolysis with surplus power from peak regulation of the power generation plant as a power supply; a fuel preparation reaction equipment con-
(Continued)

figured to produce fuel with hydrogen and carbon dioxide; an input end of the fuel preparation reaction equipment is connected to a hydrogen output pipe of an electrolytic hydrogen production device, while another input end is connected to a supply source of carbon dioxide, a fuel output port being connected to a fuel collection device or a fuel utilization device. The system can directly consume peak-regulation power from a power plant, thereby improving power grid balance and differences between peaks and valleys, while achieving phase-changed storage of electric energy and effective usage of energy.

12 Claims, 1 Drawing Sheet

(51) Int. Cl.
*C07C 29/151* (2006.01)
*C07C 31/04* (2006.01)
*H02J 3/28* (2006.01)
*H02J 15/00* (2006.01)

(58) Field of Classification Search
CPC ....... Y02E 60/366; Y02E 70/00; Y02E 70/30; C25B 1/00; C25B 1/02; C25B 1/04; C25B 15/00; C25B 15/02; C07C 29/00; C07C 29/15; C07C 29/151; C07C 31/00; C07C 31/02; C07C 31/04
See application file for complete search history.

(56) References Cited

FOREIGN PATENT DOCUMENTS

| | | |
|---|---|---|
| CN | 204633478 U | 9/2015 |
| CN | 106230349 A | 12/2016 |

OTHER PUBLICATIONS

English translation of the Written Opinion of the International Search Authority in the international application No. PCT/CN2017/099592, dated Nov. 1, 2017.
Supplementary European Search Report in the European application No. 17915443.0, dated Sep. 29, 2020.

\* cited by examiner

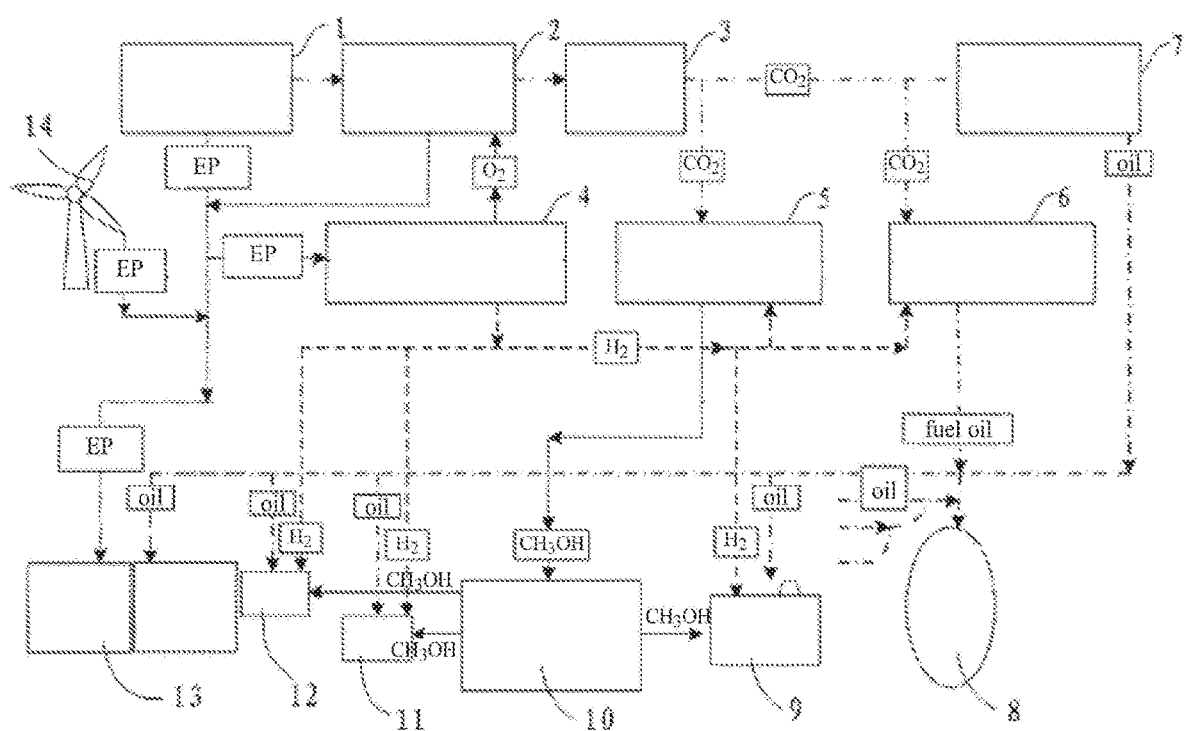

FUEL PREPARATION REACTION SYSTEM, PEAK REGULATION SYSTEM FOR POWER GENERATION PLANT AND POWER GENERATION PLANT

CROSS-REFERENCE TO RELATED APPLICATIONS

The present application is a national stage of International Application No. PCT/CN2017/099592 filed on Aug. 30, 2017, published as WO 2019/000622, which claims priority to Chinese Patent Application No. 201710516756.5 filed on Jun. 29, 2017. The disclosures of these applications are hereby incorporated by reference in their entirety.

TECHNICAL FIELD

The present disclosure relates to field of electric power (EP) energy, and in particular to a reaction system for producing fuel, a system for regulating a peak load of a power plant that includes the reaction system for producing fuel, and a power plant.

BACKGROUND

At present, a state electric power system is rich of power yield, yet lacks power of a regulatable peak load, such as a gas turbine, pumped storage, etc. There is a major issue between regulation of a peak load of a grid and flexibility of a thermal power unit. A grid lacks capability to absorb new energy such as wind power, photovoltaic power, hydro-power, nuclear power, etc.

In related art, a major issue in operation of a grid has been regulation of a peak load of a thermal power plant. At present, all transformation for flexible regulation of a peak load of domestic thermal power is directed at a unit for heating in winter. A problem facing many thermal power plants is how to regulate a peak load in summer. Reform for in-depth peak load regulation is inevitable in order to meet a demand for regulating a peak load of a grid, minimizing energy waste during peak load regulation, and for a power plant to survive fierce competition.

Accordingly, a pressing need is how to avoid energy waste in regulating a peak load of a power plant.

SUMMARY

In view of this, embodiments herein provide a reaction system for producing fuel, capable of using energy efficiently, avoiding loss of electric energy during peak load regulation.

Embodiments herein further provide a system for regulating a peak load of a power plant that includes the reaction system for producing fuel, and a power plant.

To that end, embodiments herein provide a technical solution as follows.

A reaction system for producing fuel includes a device for producing hydrogen by electrolysis and a reactor for producing fuel.

The device for producing hydrogen by electrolysis is connected to a power supply device of a power plant. The device for producing hydrogen by electrolysis is adapted to producing hydrogen by electrolysis powered by peak load regulated power balance of the power supply device of the power plant.

The reactor for producing fuel is adapted to producing fuel using the hydrogen and carbon dioxide. A first input of the reactor for producing fuel is connected to a pipeline for outputting the hydrogen of the device for producing hydrogen by electrolysis. A second input of the reactor for producing fuel is connected to a source for supplying the carbon dioxide. A port for outputting the fuel of the reactor for producing fuel is adapted to being connected to a device for collecting the fuel or a device that may be to use the fuel.

The reactor for producing fuel may include at least one of a device for producing methanol fuel or a device for producing fuel oil.

A port for outputting the fuel of the device for producing methanol fuel may be connected to a device for storing methanol through a device for purifying methanol.

A port for outputting the fuel of the device for producing fuel oil may be connected to a facility for storing oil.

The port for outputting the fuel of the reactor for producing fuel may be connected to at least one of a source for supplying the fuel to a petrochemical system or a device for storing the fuel for a boiler of the power plant.

The pipeline for outputting the hydrogen of the device for producing hydrogen by electrolysis may be connected to a hydrogen tank of transportation equipment through a device for ultra-low temperature liquefaction or a device for high pressure gas compression, for providing the transportation equipment with ultra-low temperature liquid hydrogen energy or high pressure compressed gaseous hydrogen.

The pipeline for outputting the hydrogen of the device for producing hydrogen by electrolysis may be connected to a device for storing the hydrogen through a collection control valve.

A pipeline for outputting oxygen of the device for producing hydrogen by electrolysis may be connected to a device for supplying oxygen to a boiler of the power plant or a blast furnace of a steel mill, for low-load stable combustion and oxygen-rich combustion in the boiler of the power plant, or for supplying pure oxygen to the blast furnace of the steel mill.

At least one of the pipeline for outputting the hydrogen or the pipeline for outputting the oxygen, of the device for producing hydrogen by electrolysis, may be provided with at least one of a filter or a purifier.

The device for producing hydrogen by electrolysis may include at least one of a device for producing hydrogen by electrolyzing an alkaline aqueous solution, a device for producing hydrogen by electrolyzing a solid polymer, or a device for producing hydrogen by electrolyzing a high temperature solid oxide.

The source for supplying the carbon dioxide may be a smoke exhaust connected to a boiler of a steel mill or a boiler of the power plant. The source for supplying the carbon dioxide may be connected to the reactor for producing fuel through a system for capturing and purifying the carbon dioxide.

The system for capturing and purifying the carbon dioxide may be connected to a device for collecting the carbon dioxide.

The source for supplying the carbon dioxide may be a device for recycling the carbon dioxide from equipment for producing oil using biomass or equipment for producing oil using garbage.

The equipment for producing oil using biomass and the equipment for producing oil using garbage may be connected to equipment for storing oil or equipment for regenerating energy that generates power using oil.

A system for regulating a peak load of a power plant includes a power supply device of a power plant, and the reaction system for producing fuel. The device for producing hydrogen by electrolysis of the reaction system for producing fuel is connected to the power supply device of the power plant to acquire the peak load regulated power balance.

The power supply device of the power plant may include an output grid of generators and an inverter connected to the output grid of generators. The inverter may be connected to the device for producing hydrogen by electrolysis.

The system for regulating a peak load of a power plant may further include a localized control center of the power plant and a grid dispatch center.

The localized control center of the power plant may be adapted to controlling the peak load regulated power balance. The localized control center of the power plant may be connected to the power supply device of the power plant at a first end, and to the grid dispatch center at a second end.

The grid dispatch center may be adapted to sending a peak load regulating instruction to the localized control center of the power plant according to real-time power generation and demand for peak load regulation in an area. The localized control center of the power plant may be adapted to regulating the peak load regulated power balance according to the peak load regulating instruction.

A power plant includes at least one of the reaction system for producing fuel or the system for regulating a peak load of a power plant.

With the reaction system for producing fuel according to the present disclosure, electric energy during a period of low power usage is acquired and converted into hydrogen energy. Then, the hydrogen energy is converted, by being applied to carbon dioxide, into chemical energy in fuel, such that electric energy, which is not suitable for storage, is converted into hydrogen energy or fuel energy, which is easy to store. With the reaction system for producing fuel according to the present disclosure, peak load regulated power balance of a power plant is consumed straightforwardly, allowing use of wind power, photovoltaic power, hydropower, nuclear power, etc., that is to be discarded otherwise, relieving grid balancing and difference between peak power usage and low power usage, increasing life of power plant equipment, implementing storage of electric energy in another form, as well as stable storage and effective use of energy.

Also disclosed is a system for regulating a peak load of a power plant that includes the reaction system for producing fuel. The peak load regulated power balance of the system for regulating a peak load is converted, by the reaction system for producing fuel, into chemical energy and stored, improving energy efficiency effectively, avoiding energy waste.

Further disclosed is a power plant including the reaction system for producing fuel. Energy recycle is formed with the reaction system for producing fuel and a boiler, saving energy effectively.

BRIEF DESCRIPTION OF THE DRAWINGS

Drawings for describing embodiments herein or related art are introduced below briefly for clearer illustration of a technical solution of embodiments herein or of related art. Note that the drawings described below refer merely to embodiments herein. A person having ordinary skill in the art may acquire other drawings according to the drawings herein without creative effort.

FIG. 1 is a diagram of a reaction system for producing fuel according to the present disclosure.

Included in FIG. 1 are: a coal or gas fueled power plant 1, a steel mill and its power plant 2, a system for capturing and purifying the carbon dioxide 3, a device for producing hydrogen by electrolysis 4, a device for producing methanol fuel 5, a device for producing fuel oil 6, equipment for producing oil using biomass or garbage 7, a facility for storing oil 8, another industrial facility 9, a petrochemical industry 10, an automobile 11, an aircraft 12, a building facility 13, and equipment for generating power using a renewable resource 14.

DETAILED DESCRIPTION

Clear and complete description to a technical solution herein is given below with reference to the drawings and embodiments herein. Clearly, embodiments illustrated herein are but some, instead of all, embodiments according to the subject disclosure. Based on the embodiments herein, a person having ordinary skill in the art may acquire another embodiment without creative effort. Any such embodiment falls within the scope of the subject disclosure.

The present disclosure provides a reaction system for producing fuel, capable of using energy efficiently, avoiding loss of electric energy during peak load regulation.

The present disclosure further provides a system for regulating a peak load of a power plant that includes the reaction system for producing fuel, and a power plant.

Referring to FIG. 1, FIG. 1 is a diagram of a reaction system for producing fuel according to the present disclosure.

According to the present disclosure, a reaction system for producing fuel may apply to a power plant, and includes a device for producing hydrogen by electrolysis 4 and a reactor for producing fuel.

The device for producing hydrogen by electrolysis 4 is connected to a power supply device of the power plant. The device for producing hydrogen by electrolysis is adapted to producing hydrogen by electrolysis powered by peak load regulated power balance of the power plant. The reactor for producing fuel is adapted to producing fuel using the hydrogen and carbon dioxide. A first input of the reactor for producing fuel is connected to a pipeline for outputting the hydrogen of the device for producing hydrogen by electrolysis 4. A second input of the reactor for producing fuel is connected to a source for supplying the carbon dioxide. A port for outputting the fuel of the reactor for producing fuel is connected to a device for collecting the fuel or a device that is to use the fuel. The hydrogen referred to herein may be gaseous hydrogen, liquid hydrogen, or hydrogen energy of another form. Gaseous hydrogen is to be described below, for example. Similarly, the carbon dioxide herein may be gaseous, or liquid, or of another form.

The device for producing hydrogen by electrolysis 4 may be a device for electrolyzing water using electric energy. The device for producing hydrogen by electrolysis 4 may be provided with a power end adapted to being connected to the power supply device of the power plant. That is, Water may be electrolyzed by power output by the power supply device of the power plant. The device for producing hydrogen by electrolysis 4 may be at least one of a number of types of devices with which hydrogen can be acquired. By using the device for producing hydrogen by electrolysis 4 and the power supply device of the power plant, the peak load regulated power balance of a generator of the power plant during a period of low power usage may be used to convert the electric energy into hydrogen energy, which may be put to use.

The reactor for producing fuel may produce fuel using the hydrogen and carbon dioxide. A pipeline for inputting hydrogen into the reactor for producing fuel may be connected to a pipeline for outputting the hydrogen of the device for producing hydrogen by electrolysis 4. The reactor for producing fuel may be connected to a source for supplying the carbon dioxide. A port for outputting the fuel of the reactor for producing fuel may be connected to a device for collecting the fuel or a device that is to use the fuel. The source for supplying the carbon dioxide may be a device such as a tank storing gaseous carbon dioxide.

The reactor for producing fuel may produce fuel using hydrogen energy and carbon dioxide according to related art. Various kinds of fuel, such as methanol and fuel oil, can be produced using hydrogen energy and carbon dioxide.

With the reaction system for producing fuel according to the present disclosure, hydrogen is produced using electric energy of the power plant during a period of low power usage, and then energy in the hydrogen (i.e., hydrogen energy) is converted, by being applied to carbon dioxide, into chemical energy in fuel, such that electric energy, which is not suitable for storage, is converted into hydrogen energy or fuel energy, which is easy to store. With the reaction system for producing fuel according to the present disclosure, peak load regulated power of a power plant is consumed straightforwardly, allowing use of wind power, photovoltaic power, hydropower, nuclear power, etc., that is to be discarded otherwise, relieving grid balancing and difference between peak power usage and low power usage, increasing life of power plant equipment, implementing storage of electric energy in another form, as well as stable storage and effective use of energy.

The reactor for producing fuel may include at least one of a device for producing methanol fuel 5 or a device for producing fuel oil 6. A port for outputting the fuel of the device for producing methanol fuel 5 may be connected to a device for storing methanol through a device for purifying methanol. A port for outputting the fuel of the device for producing fuel oil 6 may be connected to a facility for storing oil.

The device for producing methanol fuel 5 may be adapted to producing methanol. The device for producing fuel oil 6 may be adapted to producing oil.

When the reactor for producing fuel is the device for producing methanol fuel 5, the device for producing methanol fuel 5 may be provided with a catalyst for a reaction that produces methanol. Therefore, the device for producing methanol fuel 5 may be provided with a channel or space for supplying the catalyst. Likewise, when the reactor for producing fuel is the device for producing fuel oil 6, it may have a catalyst for catalyzing a reaction that produces fuel oil. The reactor for producing fuel may also be another reactor device for producing fuel.

The port for outputting the fuel of the reactor for producing fuel may be connected to a source for supplying the fuel to a petrochemical system. The reactor for producing fuel may be provided with a port for outputting the fuel. The port for outputting the fuel may be adapted to being connected to a device for storing the fuel for a boiler of the power plant.

The fuel produced by the reactor for producing fuel may be used straightforwardly in a petrochemical system for energy use and storage. The fuel may be used straightforwardly in the boiler of the power plant as a source of fuel to the boiler.

The pipeline for outputting the hydrogen of the device for producing hydrogen by electrolysis 4 may be connected to a hydrogen tank of transportation equipment through a device for ultra-low temperature liquefaction or a device for high pressure gas compression, for providing the transportation equipment with ultra-low temperature liquid hydrogen energy or high pressure compressed gaseous hydrogen. Thus, the transportation equipment may be provided with liquid hydrogen energy of an ultra-low temperature (around −253 degrees) or high pressure compressed gaseous hydrogen (ranging from 0.5 MPa to 80 MPa). The pipeline for outputting the hydrogen of the device for producing hydrogen by electrolysis 4 may be connected to a device for storing the hydrogen. The device for storing the hydrogen may be adapted to storing energy. A pipeline connecting the pipeline for outputting the hydrogen to the device for storing the hydrogen may be provided with a collection control valve.

The hydrogen produced by the device for producing hydrogen by electrolysis 4 may be input straightforwardly into and used by a reactor. Hydrogen energy may be stored more easily than electric energy. Gaseous hydrogen may be stored straightforwardly. The device for ultra-low temperature liquefaction or the device for high pressure gas compression may facilitate storage of hydrogen energy. Transportation equipment may refer to an automobile, a ship, an aircraft, etc. With development of hydrogen energy technology, hydrogen energy has been used mainly in an automobile, a ship, an aircraft, etc. Transportation equipment in general may require a hydrogen tank that makes hydrogen energy portable.

A pipeline for outputting oxygen of the device for producing hydrogen by electrolysis 4 may be connected to a device for supplying oxygen to a boiler of the power plant or a blast furnace of a steel mill, for low-load stable combustion and oxygen-rich combustion in the boiler of the power plant, or for supplying pure oxygen to the blast furnace of the steel mill.

At least one of the pipeline for outputting the hydrogen or the pipeline for outputting the oxygen, of the device for producing hydrogen by electrolysis 4, may be provided with at least one of a filter or a purifier.

The device for producing hydrogen by electrolysis 4 may produce both hydrogen and oxygen. Both oxygen and hydrogen in a gaseous state, for example, may be common in industry. Both the oxygen and the hydrogen produced herein may be filtered and purified to increase purity thereof, avoiding impact of impurity, allowing better use of the oxygen and the hydrogen produced.

The device for producing hydrogen by electrolysis 4 may include at least one of a device for producing hydrogen by electrolyzing an alkaline aqueous solution, a device for producing hydrogen by electrolyzing a solid polymer, or a device for producing hydrogen by electrolyzing a high temperature solid oxide.

Electric energy of the device for producing hydrogen by electrolysis 4, that is, electric energy of at least one of a device for producing hydrogen by electrolyzing an alkaline aqueous solution, a device for producing hydrogen by electrolyzing a solid polymer, or a device for producing hydrogen by electrolyzing a high temperature solid oxide, may come from the power supply device of the power plant. A source of water of a device for electrolyzing an alkaline aqueous solution and of a device for electrolyzing a solid polymer may come from waste water of a boiler or condensate of a boiler system. A source of water of a device for electrolyzing a high temperature solid oxide may come from high temperature main steam of the power plant.

The device for producing hydrogen by electrolysis 4 may be provided with a pipeline for outputting oxygen. The pipeline for outputting oxygen may be adapted to being connected to a device for supplying oxygen to a boiler of the power plant. The device for producing hydrogen by electrolysis 4 may generate both hydrogen and oxygen. The oxygen may be used in oxygen-rich combustion in a combustion chamber of the boiler of the power plant. Combustion in a boiler in general may require a supply of oxygen. The oxygen output by the device for producing hydrogen by electrolysis 4 may be used in low-load oxygen-rich combustion and stable combustion in a boiler, increasing capacity of a boiler of a unit in peak load regulated operation.

The pipeline for outputting the oxygen may be provided with an impurity filter.

The pipeline for outputting the oxygen may be connected to a boiler. A source of water of the device for producing hydrogen by electrolysis 4 may come from condensate of a boiler. The condensate may be electrolyzed to form hydrogen and oxygen. The hydrogen may be used in synthesis of fuel, which may be used in a fuel furnace of a boiler. The oxygen may be used to ensure oxygen-rich combustion in a boiler.

The source for supplying the carbon dioxide may be provided with a system for capturing and purifying the carbon dioxide 3. The system for capturing and purifying the carbon dioxide may be adapted to purifying carbon dioxide. The system for capturing and purifying the carbon dioxide 3 may be connected to a device for collecting the carbon dioxide.

The source for supplying the carbon dioxide may be a smoke exhaust system connected to a boiler of the power plant.

The source for supplying the carbon dioxide may be a smoke exhaust connected to a boiler of a steel mill or a boiler of the power plant. The source for supplying the carbon dioxide may be connected to the reactor for producing fuel through a system for capturing and purifying the carbon dioxide 3. The system for capturing and purifying the carbon dioxide 3 may be connected to a device for collecting the carbon dioxide.

The source for supplying the carbon dioxide may use ready carbon dioxide.

The source for supplying the carbon dioxide may also use carbon dioxide in exhaust gas of a boiler, saving cost of carbon dioxide and recycling exhaust of the boiler, reducing emission of carbon dioxide, avoiding energy waste. The system for capturing and purifying the carbon dioxide 3 may be adapted to filtering and purifying exhaust of a boiler, and supplying acquired carbon dioxide to the reactor for producing fuel. The device for collecting the carbon dioxide may store carbon dioxide that takes no part in the reaction for the moment.

The source for supplying the carbon dioxide may be a device for recycling carbon dioxide exhaust. A smoke exhaust of the source for supplying the carbon dioxide may also be connected to equipment for producing oil using biomass or equipment for producing oil using garbage. The equipment for producing oil using biomass and or the equipment for producing oil using garbage may be connected to equipment for storing oil or equipment for regenerating energy that generates power using oil.

The source for supplying the carbon dioxide may be a device for recycling carbon dioxide exhaust. The carbon dioxide may also come from equipment for producing oil using biomass or equipment for producing oil using garbage. The equipment for producing oil using biomass and or the equipment for producing oil using garbage may be connected to equipment for storing oil or equipment for regenerating energy that generates power using oil.

Referring to FIG. 1, the equipment for producing oil using biomass or garbage 7 in FIG. 1 may include equipment for producing oil using biomass or equipment for producing oil using garbage, capable of reacting using collected carbon dioxide to acquire and store oil.

The device for producing hydrogen by electrolysis 4 may also be connected to a device for producing purified water of a workshop for processing chemical water of the power plant. The device for producing hydrogen by electrolysis may use water resources formed by the device for producing purified water as a source of water. A water circulating loop may form among the device for producing hydrogen by electrolysis 4, a device for producing purified water, a boiler, and a steam turbine. For example, a pipeline of source of water of the device for producing hydrogen by electrolysis 4 may be connected to a steam turbine of a boiler, such that hydrogen may be produced by electrolysis using condensate of the steam turbine.

Carbon dioxide may be extracted and stored using a steel mill and its power plant 2.

With the reaction system for producing fuel according to the present disclosure, a device for producing hydrogen by electrolysis may be powered through an inverter using electricity during a period of low power usage to produce massive amount of gaseous hydrogen of high purity. A smoke exhaust of a boiler of an oil factory, a power plant, a steel mill, an owned power plant, etc., may be provided with a system for collecting carbon dioxide to produce carbon dioxide of high concentration. Different kinds of liquid fuel such as methanol, fuel oil, etc., may be synthesized by the reactor for producing fuel respectively under different temperatures and pressures using different catalysts. The above two kinds of liquid fuel may be used as raw material for petrochemical industry, or as fuel for construction and transportation facilities, or be fed to a boiler to be combined with pure oxygen generated in a hydrogen production process, so as to implement carbon neutral operation and oxygen-rich combustion in a pyrolysis oil plant, a power plant, a steel mill, etc. With the reaction system for producing fuel according to the present disclosure, damage to power plant equipment caused by imbalance between peak power usage and low power usage of a power plant is relieved greatly; electric energy, which is hard to store, is converted successfully into hydrogen energy or chemical energy, which is then stored, implementing effective storage of energy, saving energy.

Refer to related art for a structure of a remaining part of the reaction system for producing fuel according to the embodiments, which will not be elaborated herein. A system for regulating a peak load of a power plant that includes the reaction system for producing fuel is further disclosed herein. The system for regulating a peak load of a power plant includes a power supply device of the power plant, and further includes the reaction system for producing fuel according to an embodiment herein. The device for producing hydrogen by electrolysis 4 of the reaction system for producing fuel is connected to the power supply device of the power plant to acquire peak load regulated power balance.

The power supply device of the power plant may include an output grid of generators and an inverter connected to the output grid of generators. The inverter may be connected to the device for producing hydrogen by electrolysis.

The power supply device of the power plant may be connected to a localized control center of the power plant adapted to controlling the peak load regulated power balance. The localized control center of the power plant may be connected to a grid dispatch center. The grid dispatch center may send a peak load regulating instruction to the localized control center of the power plant according to real-time power generation and demand for peak load regulation in an area. The localized control center of the power plant may regulate the peak load regulated power balance according to the peak load regulating instruction, and transport the peak load regulated power balance to the power supply device of the power plant.

The localized control center of the power plant may be adapted to controlling the peak load regulated power balance. The localized control center of the power plant may be connected to the power supply device of the power plant at a first end, and to the grid dispatch center at a second end. The grid dispatch center may be adapted to sending a peak load regulating instruction to the localized control center of the power plant according to real-time power generation and demand for peak load regulation in an area. The localized control center of the power plant may be adapted to regulating the peak load regulated power balance according to the peak load regulating instruction.

The power supply device of the power plant may include an output grid of generators and an inverter. The grid dispatch center may be adapted to instructing the localized control center of the power plant to perform peak load regulation. The grid dispatch center may be connected to the localized control center of the power plant for controlling power supply. The inverter may be connected to the localized control center of the power plant and the device for producing hydrogen by electrolysis.

Referring to FIG. 1, equipment such as the grid dispatch center, the inverter, etc., may be included in a coal or gas fueled power plant 1. The coal or gas fueled power plant 1 may be connected to an output grid of generators of the coal or gas fueled power plant 1. The output grid of generators may be a generator. A steam turbine of a boiler may be connected to the generator. The generator may be a source of electric energy during peak load regulation. The inverter may transport the electric energy of the generator to the device for producing hydrogen by electrolysis to power the electrolysis.

The above system may include a grid and a platform for controlling peak load regulation of the power plant. The grid and the platform for controlling peak load regulation of the power plant may include a grid dispatch center and a localized control center of the power plant. The grid dispatch center may instruct the localized control center of the power plant to perform peak load regulation and regulate a peak load according to real-time generation of wind power photovoltaic power and demand for peak load regulation in an area. By controlling an electric switch circuit connected between the generator and the inverter, the localized control center of the power plant may control the inverter to convert a direct current of the generator into an alternating current, which may be used to power the device for producing hydrogen by electrolysis.

Also disclosed is a power plant, which includes at least one of the reaction system for producing fuel or the system for regulating a peak load of a power plant.

Electric power energy acquired herein may be provided, through a grid circuit, as power or power storage, to a facility such as one related to a petrochemical industry 10, an automobile 11, an aircraft 12, another industrial facility 9, another social facility 13, etc., which is not elaborated herein.

Fuel oil produced by the reaction system for producing fuel may be supplied to a facility for storing oil 8 through a pipeline for supplying oil thereto, such as an oil storage pipeline, an underground oil depot, etc. The fuel oil may also be supplied to a facility related to a petrochemical industry 10, an automobile 11, an aircraft 12, another industrial facility 9, another building facility 13, etc.

Hydrogen energy produced herein may likewise be supplied to an automobile 11, an aircraft 12, etc. The hydrogen energy may be supplied to another industrial facility 9 through a supply pipeline or equipment.

In addition, electric energy of the power supply device of a power plant may be generated using various forms of power, including various types of renewable energy. Power may be generated using equipment for generating power using renewable energy 14, and supplied to the power supply device of the power plant.

Embodiments herein are described progressively, each focusing on what differs from the others. Refer to one another for identical or similar parts among the embodiments.

Elaborated above are the reaction system for producing fuel, the system for regulating a peak load of a power plant, and the power plant according to the present disclosure. The principle and implementation of the present disclosure are illustrated with reference to specific examples. The embodiments are described merely to facilitate understanding of the method of the present disclosure and the concept thereof. Note that a person having ordinary skill in the art may make various modification and variations without departing from the principle of the subject disclosure. Such modification and variations also fall in the protection scope of the subject disclosure.

The invention claimed is:

1. A reaction system for producing fuel, comprising a device for producing hydrogen by electrolysis and a reactor for producing fuel,
   wherein the device for producing hydrogen by electrolysis is connected to a power supply device of a power plant,
   wherein the device for producing hydrogen by electrolysis is adapted to producing hydrogen by electrolysis powered by peak load regulated power balance of the power supply device of the power plant,
   wherein the reactor for producing fuel is adapted to producing fuel using the hydrogen and carbon dioxide, wherein a first input of the reactor for producing fuel is connected to a pipeline for outputting the hydrogen of the device for producing hydrogen by electrolysis, wherein a second input of the reactor for producing fuel is connected to a source for supplying the carbon dioxide, wherein a port for outputting the fuel of the reactor for producing fuel is adapted to being connected to a device for collecting the fuel or a device that is to use the fuel,
   wherein the pipeline for outputting the hydrogen of the device for producing hydrogen by electrolysis is connected to at least one of:
   a hydrogen tank of transportation equipment, through a device for ultra-low temperature liquefaction or a device for high pressure gas compression, for providing the transportation equipment with ultra-low temperature liquid hydrogen energy or high pressure compressed gaseous hydrogen; or
   a device for storing the hydrogen, through a collection control valve,
   wherein a pipeline for outputting oxygen of the device for producing hydrogen by electrolysis is connected to a device for supplying oxygen to a boiler of the power plant or a blast furnace of a steel mill, for low-load stable combustion and oxygen-rich combustion in the boiler of the power plant, or for supplying pure oxygen to the blast furnace of the steel mill.

2. The reaction system of claim 1, wherein the reactor for producing fuel comprises at least one of a device for producing methanol fuel or a device for producing fuel oil,
wherein a port for outputting the fuel of the device for producing methanol fuel is connected to a device for storing methanol through a device for purifying methanol,
wherein a port for outputting the fuel of the device for producing fuel oil is connected to a facility for storing oil.

3. The reaction system of claim 2, wherein the port for outputting the fuel of the reactor for producing fuel is connected to at least one of a source for supplying the fuel to a petrochemical system or a device for storing the fuel for a boiler of the power plant.

4. The reaction system of claim 1, wherein at least one of the pipeline for outputting the hydrogen or the pipeline for outputting the oxygen, of the device for producing hydrogen by electrolysis, is provided with at least one of a filter or a purifier.

5. The reaction system of claim 1, wherein the device for producing hydrogen by electrolysis comprises at least one of a device for producing hydrogen by electrolyzing an alkaline aqueous solution, a device for producing hydrogen by electrolyzing a solid polymer, or a device for producing hydrogen by electrolyzing a high temperature solid oxide.

6. The reaction system of claim 1, wherein the source for supplying the carbon dioxide is a smoke exhaust connected to a boiler of a steel mill or a boiler of the power plant, wherein the source for supplying the carbon dioxide is connected to the reactor for producing fuel through a system for capturing and purifying the carbon dioxide,
and/or wherein the system for capturing and purifying the carbon dioxide is connected to a device for collecting the carbon dioxide.

7. The reaction system of claim 1, wherein the source for supplying the carbon dioxide is a device for recycling the carbon dioxide from equipment for producing oil using biomass or equipment for producing oil using garbage,
wherein the equipment for producing oil using biomass and the equipment for producing oil using garbage are connected to equipment for storing oil or equipment for regenerating energy that generates power using oil.

8. A system for regulating a peak load of a power plant, comprising a reaction system for producing fuel and a power supply device of the power plant,
wherein the reaction system comprises a device for producing hydrogen by electrolysis and a reactor for producing fuel,
wherein the device for producing hydrogen by electrolysis is connected to the power supply device of the power plant, wherein the device for producing hydrogen by electrolysis is adapted to producing hydrogen by electrolysis powered by peak load regulated power balance of the power supply device of the power plant,
wherein the reactor for producing fuel is adapted to producing fuel using the hydrogen and carbon dioxide, wherein a first input of the reactor for producing fuel is connected to a pipeline for outputting the hydrogen of the device for producing hydrogen by electrolysis, wherein a second input of the reactor for producing fuel is connected to a source for supplying the carbon dioxide, wherein a port for outputting the fuel of the reactor for producing fuel is adapted to being connected to a device for collecting the fuel or a device that is to use the fuel,
wherein the device for producing hydrogen by electrolysis of the reaction system is connected to the power supply device of the power plant to acquire the peak load regulated power balance,
wherein the pipeline for outputting the hydrogen of the device for producing hydrogen by electrolysis is connected to at least one of:
a hydrogen tank of transportation equipment, through a device for ultra-low temperature liquefaction or a device for high pressure gas compression, for providing the transportation equipment with ultra-low temperature liquid hydrogen energy or high pressure compressed gaseous hydrogen; or
a device for storing the hydrogen, through a collection control valve,
wherein a pipeline for outputting oxygen of the device for producing hydrogen by electrolysis is connected to a device for supplying oxygen to a boiler of the power plant or a blast furnace of a steel mill, for low-load stable combustion and oxygen-rich combustion in the boiler of the power plant, or for supplying pure oxygen to the blast furnace of the steel mill.

9. The system for regulating a peak load of a power plant of claim 8, wherein the power supply device of the power plant comprises an output grid of generators and an inverter connected to the output grid of generators, wherein the inverter is connected to the device for producing hydrogen by electrolysis.

10. The system for regulating a peak load of a power plant of claim 8, further comprising a localized control center of the power plant and a grid dispatch center,
wherein the localized control center of the power plant is adapted to controlling the peak load regulated power balance, wherein the localized control center of the power plant is connected to the power supply device of the power plant at a first end, and to the grid dispatch center at a second end,
wherein the grid dispatch center is adapted to sending a peak load regulating instruction to the localized control center of the power plant according to real-time power generation and demand for peak load regulation in an area, wherein the localized control center of the power plant is adapted to regulating the peak load regulated power balance according to the peak load regulating instruction.

11. A power plant, comprising the system for regulating a peak load of a power plant according to claim 8.

12. A power plant, comprising a reaction system for producing fuel, the reaction system comprising a device for producing hydrogen by electrolysis and a reactor for producing fuel,
wherein the device for producing hydrogen by electrolysis is connected to a power supply device of a power plant, wherein the device for producing hydrogen by electrolysis is adapted to producing hydrogen by electrolysis powered by peak load regulated power balance of the power supply device of the power plant,
wherein the reactor for producing fuel is adapted to producing fuel using the hydrogen and carbon dioxide, wherein a first input of the reactor for producing fuel is connected to a pipeline for outputting the hydrogen of the device for producing hydrogen by electrolysis, wherein a second input of the reactor for producing fuel is connected to a source for supplying the carbon dioxide, wherein a port for outputting the fuel of the reactor for producing fuel is adapted to being connected to a device for collecting the fuel or a device that is to use the fuel, wherein the pipeline for outputting the hydrogen of the device for producing hydrogen by electrolysis is connected to at least one of:

a hydrogen tank of transportation equipment, through a device for ultra-low temperature liquefaction or a device for high pressure gas compression, for providing the transportation equipment with ultra-low temperature liquid hydrogen energy or high pressure compressed gaseous hydrogen; or a device for storing the hydrogen, through a collection control valve, wherein a pipeline for outputting oxygen of the device for producing hydrogen by electrolysis is connected to a device for supplying oxygen to a boiler of the power plant or a blast furnace of a steel mill, for low-load stable combustion and oxygen-rich combustion in the boiler of the power plant, or for supplying pure oxygen to the blast furnace of the steel mill.

* * * * *